(12) United States Patent
Yang et al.

(10) Patent No.: US 11,523,790 B2
(45) Date of Patent: Dec. 13, 2022

(54) SYSTEMS, METHODS, COMPUTING DEVICES, AND STORAGE MEDIA FOR MEDICAL EXAMINATION

(71) Applicant: SHANGHAI UNITED IMAGING HEALTHCARE CO., LTD., Shanghai (CN)

(72) Inventors: Le Yang, Shanghai (CN); Haihua Zhou, Shanghai (CN); Shurui Zhao, Shanghai (CN); Jing Yan, Shanghai (CN); Na Zhang, Shanghai (CN); Chunhua Jiang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 93 days.

(21) Appl. No.: 17/095,712

(22) Filed: Nov. 11, 2020

(65) Prior Publication Data
US 2021/0059628 A1 Mar. 4, 2021

Related U.S. Application Data

(63) Continuation of application No. PCT/CN2019/086671, filed on May 13, 2019.

(30) Foreign Application Priority Data

May 11, 2018 (CN) .......................... 201810450563.9

(51) Int. Cl.
*A61B 6/00* (2006.01)
(52) U.S. Cl.
CPC .............. *A61B 6/5264* (2013.01); *A61B 6/40* (2013.01); *A61B 6/44* (2013.01); *A61B 6/54* (2013.01)

(58) Field of Classification Search
CPC ....... A61B 6/5258; A61B 6/486; A61B 5/093; A61B 5/02405; A61B 5/02; A61B 5/0059; A61B 5/0816; A61B 5/486
See application file for complete search history.

(56) References Cited

U.S. PATENT DOCUMENTS

| | | |
|---|---|---|
| 2005/0119560 A1 | 6/2005 | Mostafavi |
| 2010/0142670 A1 | 6/2010 | Saito et al. |

(Continued)

FOREIGN PATENT DOCUMENTS

| | | |
|---|---|---|
| CN | 103845070 A | 6/2014 |
| CN | 105078493 A | 11/2015 |

(Continued)

OTHER PUBLICATIONS

The Extended European Search Report in European Application No. 19798938.7 dated May 11, 2021, 6 pages.

(Continued)

*Primary Examiner* — Don K Wong
(74) *Attorney, Agent, or Firm* — Metis IP LLC (57) ABSTRACT

The present disclosure relates to systems, methods, computing devices, and storage media for medical examination. The medical examination system comprises: a breathing guiding apparatus configured to guide a breathing of a subject; an imaging device configured to scan the subject; and a controller coupled to the breathing guiding apparatus and configured to cause the breathing guiding apparatus to generate a breath guiding state for guiding the breathing of the subject.

20 Claims, 3 Drawing Sheets (56) References Cited

U.S. PATENT DOCUMENTS

| | | |
|---|---|---|
| 2011/0082348 A1 | 4/2011 | Herold |
| 2014/0055133 A1 | 2/2014 | I et al. |
| 2016/0081613 A1 | 3/2016 | Braun et al. |
| 2018/0117359 A1 | 5/2018 | Hale |

FOREIGN PATENT DOCUMENTS

| | | | |
|---|---|---|---|
| CN | 106859678 A | | 6/2017 |
| JP | 2012085915 A | * | 5/2012 |
| WO | 2019214744 A1 | | 11/2019 |

OTHER PUBLICATIONS

First Office Action in Chinese Application No. 201810450563.9 dated Dec. 2, 2019, 25 pages.
International Search Report in PCT/CN2019/086671 dated Jul. 29, 2019, 4 pages.
Written Opinion in PCT/CN2019/086671 dated Jul. 29, 2019, 5 pages.

* cited by examiner

SYSTEMS, METHODS, COMPUTING DEVICES, AND STORAGE MEDIA FOR MEDICAL EXAMINATION

CROSS-REFERENCE TO RELATED APPLICATIONS

This application is a continuation of International Patent Application No. PCT/CN2019/086671, filed on May 13, 2019, which claims priority to Chinese Application No. 201810450563.9 filed on May 11, 2018, the contents of which are incorporated herein by reference.

TECHNICAL FIELD

The present disclosure relates to medical imaging, and more particularly relates to systems, methods, computing devices, and storage media for imaging based medical examination.

BACKGROUND

In the medical field, examinations based on imaging technologies, such as CT, MR, and PET, have advanced tremendously. In an imaging process, it is desirable for a patient to keep stationary as long as possible so as to reduce motion artifacts in an acquired image. Even so, a patient cannot be in an absolute stationary state because one or more portions of the patient may undergo vital and/or physiological movement due to, such as breathing. Therefore, removing or reducing motion artifacts brought about by such vital and/or physiological movement has always been a focus of related researches.

However, current technical solutions for reducing motion artifacts in medical imaging include processing, by separation and/or certain algorithms, image information acquired by scanning a subject using a device so as to reduce motion artifacts existing in the process of medical examination. Conventional solutions often involve an accurate image acquisition apparatus and a complicated algorithm. There may be a large amount of data to be processed in a medical examination, which results in a huge workload. In addition, differences between images to be processed and processed images are tiny such that it is difficult to tell them apart.

SUMMARY

In view of the above limitations, it is desirable to provide a system, method, computing device, and storage media configured to reduce or remove motion artifacts in medical examination.

A medical examination system, including: a breathing guiding apparatus configured to guide a breathing of a subject; an imaging device configured to scan the subject; and a controller coupled to the breathing guiding apparatus and configured to cause the breathing guiding apparatus to generate a breath guiding state for guiding the breathing of the subject.

In some embodiments, the breathing guiding apparatus includes a light source electrically connected to the controller, the light source being configured to generate, under the control of the controller, lights that guide the breathing of the subject.

In some embodiments, the controller is configured to activate the imaging device based on time determined by the breathing guiding apparatus.

In some embodiments, the medical examination system further includes a breathing synchronization detection apparatus coupled to the controller, the breathing synchronization detection apparatus being configured to detect whether the breathing of the subject is consistent with the breath guiding state generated by the breathing guiding apparatus.

In some embodiments, the breathing synchronization detection apparatus includes a sensor configured to sense the breathing of the subject when the subject is at a scanning position.

In some embodiments, the breathing synchronization detection apparatus further includes an image acquisition device.

In some embodiments, the breathing synchronization detection apparatus further includes a slip ring, wherein the image acquisition device is set on an inner side wall of the slip ring.

In some embodiments, the imaging device includes an X-ray generator, the controller is coupled to the X-ray generator, and the X-ray generator is configured to emit X-rays at a time point when an inhalation or an exhalation of the subject ends.

In some embodiments, the imaging device further includes a slip ring, wherein the X-ray generator is amounted on the slip ring.

A method implemented on a computing device having at least one processor and at least one computer-readable storage device, wherein the method comprising: generating a first light pattern guiding a subject to inhale and a second light pattern guiding the subject to exhale; causing an imaging device to image the subject when the subject breathes under a guidance of the first light pattern and the second light pattern; and generating an image of the subject based on data of the subject generated by the imaging device.

In some embodiments, the imaging device includes an X-ray detector, the method further comprising: obtaining a determination result by detecting whether breathing of the subject is consistent with a breath guiding state generated by a breathing guiding apparatus; and in response to a determination result that the breathing of the subject is consistent with the breath guiding state generated by the breathing guiding apparatus, causing the X-ray generator to generate X-rays.

In some embodiments, the method further comprising: in response to a determination result that the breathing of the subject is inconsistent with the breath guiding state generated by the breathing guiding apparatus, instructing the subject to adjust the breathing according to the breathing guiding state until the breathing of the subject becomes consistent with the breath guiding state generated by the breathing guiding apparatus; and causing the X-ray generator to generate X-ray.

In some embodiments, the method further comprising: in response to a determination result that the breathing of the subject is consistent with the breath guiding state generated by the breathing guiding apparatus, causing the X-ray generator to generate X-rays at time points when at least one of the first light pattern or the second light pattern ends.

In some embodiments, a ratio of a duration of the first light pattern to a duration of the second light pattern ranges from 1:1.5 to 1:2.

In some embodiments, the first light pattern and the second light pattern are activated alternately.

In some embodiments, a strength of the first light pattern changes from weak to strong, and a strength of the second light pattern changes from strong to weak.

A computing device includes storage, a processor, and computer programs stored on the storage and executable by the processor, and the processor implements the steps of the medical examination method when the computer programs are executed.

A computing device, comprising: storage; a processor; and computer programs stored in the storage and executable by the processor, wherein, the processor executes the computer programs to implement the methods disclosed herein.

A computer readable storage medium storing computer programs, wherein, when the computer programs are executed by a processor, the methods disclosed herein may be implemented.

The present disclosure provides a system, method, computing device, and storage medium for medical examination. The medical examination system may include a breathing guiding apparatus, an imaging device (e.g., an X-ray generator), and a controller. The breathing guiding apparatus in the medical examination system may guide a subject to adjust his/her breathing rhythm according to a breath guiding state (e.g., the breath guiding state including a regular breathing rhythm). After the subject adjusts the rhythm of breathing, the medical examination system may perform imaging using the imaging device (e.g., an X-ray scanning using the X-ray generator). The medical examination system is capable of guiding the subject to be scanned to breathe regularly. The medical examination system is capable of acquiring a medical examination image of the subject to be scanned at a time point when an inhalation of the subject ends and/or a time point when an exhalation of the subject ends. The medical examination system can reduce motion artifacts due to breathing during a scanning process, such that the examination based on the obtained image(s) may be more stable and reliable.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

Description of reference signs in the figures: medical examination system 10; slip ring 101; patient support 102; breathing guiding apparatus 100; X-ray generator 200; controller 300; breathing synchronization detection apparatus 400; computer device 20; storage 21; processor 22; computer program 23.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 2:
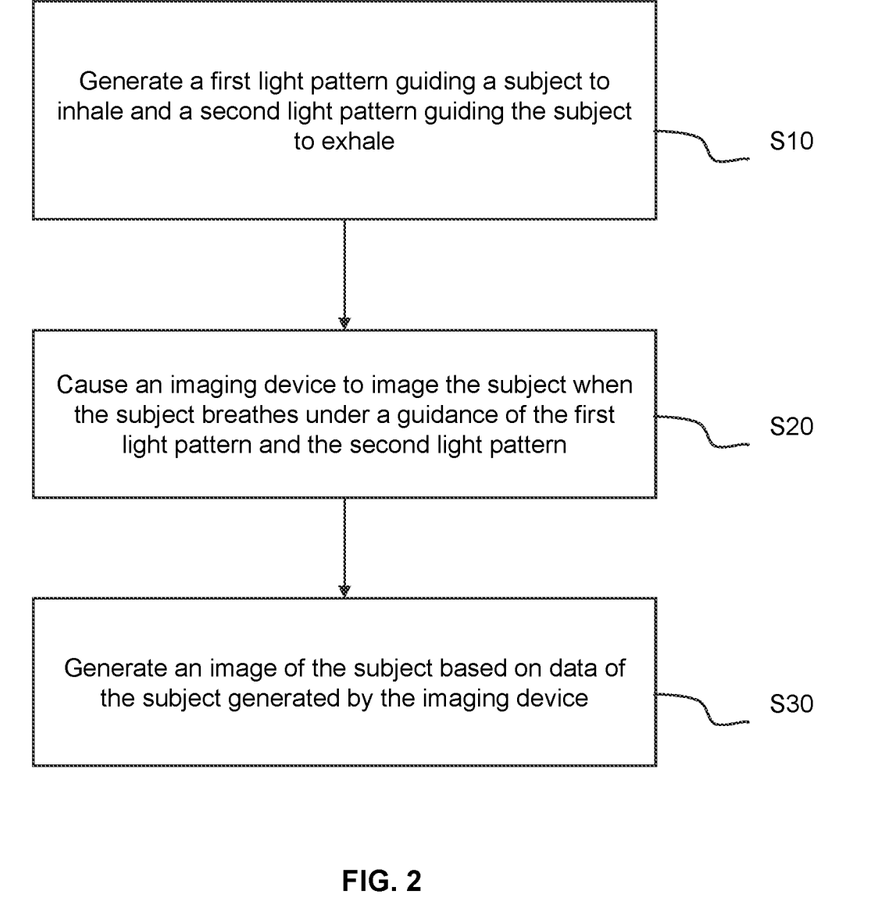
FIG. 2 is a flow chart of an exemplary medical examination process according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging, such as for disease diagnosis or research purposes. In some embodiments, the imaging system may be a computed tomography (CT) system, a magnetic resonance imaging (MRI) system, a computed tomography-positron emission tomography (CT-PET) system, an emission computed tomography (ECT) system, a computed tomography-magnetic resonance imaging (CT-MM) system, an ultrasonography system, an X-ray photography system, or the like, or any combination thereof.

Figure 1:
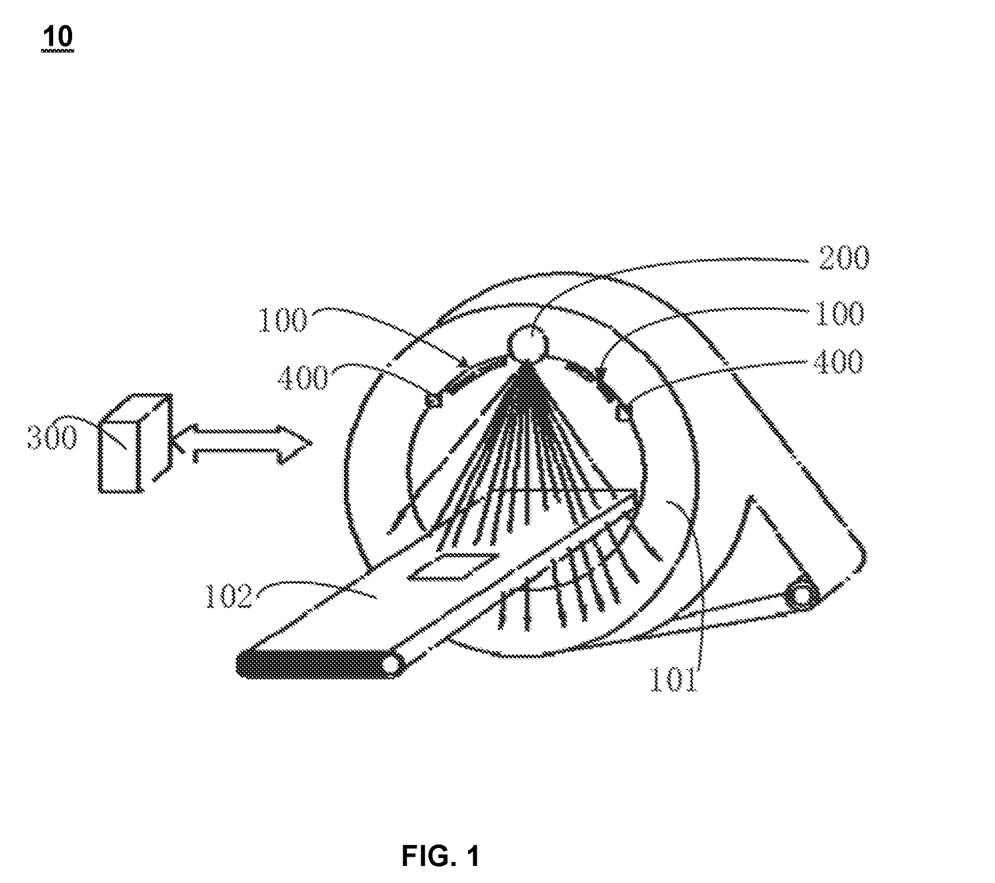
FIG. 1 illustrates an exemplary medical examination system according to some embodiments of the present disclosure.

Referring to FIG. 1, a medical examination system 10 is provided. The medical examination system 10 includes a breathing guiding apparatus 100, an X-ray generator 200, and a controller 300. It is understood that the X-ray generator 200 is a non-limiting example of an imaging device suitable for the systems and methods of the present disclosure. Other exemplary imaging devices suitable for the systems and methods disclosed herein may include magnetic resonance (MR) scanner, positron emission computed tomography (PET) scanner, or the like, or any combination thereof.

The breathing guiding apparatus 100 is configured to guide breathing of a subject (e.g., a patient) to be scanned or being scanned. The breathing guiding apparatus 100 may be set at a position where the subject can see. For example, the breathing guiding apparatus 100 may be set on a slip ring 101 of the medical examination system 10. In some embodiments, the breathing guiding apparatus 100 is set at a place that does not interfere with normal operations of the medical examination system 10. The position of the breathing guiding apparatus 100 is not specifically limiting as long as the function of guiding the breathing of the subject can be implemented. As another example, the subject may lie on a patient support 102. A medical staff may control, through the controller 300, the breathing guiding apparatus 100 to generate a breath guiding state to guide the breathing of the subject to a regular state.

The X-ray generator 200 may be embedded in the slip ring 101 of the medical examination system 10. The X-ray generator 200 may be configured to generate X-rays to perform a scanning process of the subject. The X-ray generator 200 may include an X-ray high voltage generator and an X-ray tube. The X-ray high voltage generator may generate a tube voltage and a tube current. The X-ray tube may generate X-rays for scanning the subject. The controller 300 may control the X-ray generator 200 to generate X-rays. For example, the controller 300 may control the X-ray generator 200 to generate X-rays of different intensities, at different irradiating times, and/or to different irradiating areas.

The controller 300 may be coupled to the breathing guiding apparatus 100. For example, the controller 300 may be operably or electrically coupled to the breathing guiding apparatus 100. The controller 300 is configured to control the breathing guiding apparatus 100 to generate a guiding state that guides the subject to breathe regularly. The controller 300 is coupled to the X-ray generator 200. For example, the subject lies on the patient support 102. The medical care staff may control the breathing guiding apparatus 100 to generate a guiding state of regular breathing through the controller 300 to guide the breathing state of the subject to be regular. After the breathing guiding apparatus 100 is turned on for a certain period of time, the breathing state of the subject may become relatively regular. Relatively regular breathing refers that the time taken for each inhalation or exhalation is almost the same. For example, the time taken for inhalation in a first breathing cycle of the subject is the same as the time taken for inhalation in a second breathing cycle. The controller 300 may control the X-ray generator 200 to generate X-rays to scan the subject. When the breathing state of the subject is relatively regular, the X-ray generator 200 may set a fixed irradiating period. The subject can breathe regularly at a fixed frequency. During an irradiating period of the X-ray generator 200, a certain rotating speed of the X-ray tube may be set. The rotating speed of the X-ray tube of the X-ray generator 200 may match the breathing frequency of the subject. In some embodiments, the controller 300 may activate the X-ray generator 200 based on the time that the breathing guiding apparatus 100 instructs the breathing of the subject. The time that the breathing guiding apparatus 100 instructs the breathing of the subject may be an empirical value, which may be set by a doctor.

The medical examination system 10 may include the breathing guiding apparatus 100, the X-ray generator 200, and the controller 300. The breathing guiding apparatus 100 in the medical examination system 10 may direct the subject to make adjustments to the breathing according to a fixed rhythm. After the subject adjusts the frequency of the breathing, the medical examination system 10 may perform an X-ray scanning using the X-ray generator 200. The medical examination system 10 may generate a plurality of scanning images. Image analysis and image processing are performed on the plurality of scanning images, and images that have less or no motion artifacts may be selected using, for example, a particular algorithm, thus improving the efficiency and/or reliability of examination performed on the medical examination system 10 overall.

In some embodiments, the breathing guiding apparatus 100 may include a light source.

The light source is used to generate lights that guide the subject to breathe at a fixed frequency. The light source may be a lamp bead, or a plurality of beads arranged at intervals. The light source is coupled to the controller 300, such as by electrical connection. The controller 300 may send a control signal to the light source to control the light source to be turned on or off and/or the duration during which the light source to be turned on and/or the intensity of the lights. The brightness of the light source may change gradually, and the lights of the light source may have different colors. The controller 300 may control the light source to light up in a time period T1, and control the light source to light out in a time period T2. The breathing state of the subject may be guided by controlling the duration of the time period T1 and the time period T2. In addition, the controller 300 may control the light source to generate lights of different frequencies and/or different light intensities. For example, the controller 300 may control the light source to emit lights of soft blue, light yellow or white. In one embodiment, the light color may be variable, and the light brightness may also vary gradually.

The breathing guiding apparatus 100 may also set a light pattern to guide exhalation or inhalation. In some embodiments, the light pattern is realized by light strips. The light strips may be made of transparent materials. The light strips may also be partial-transparent material. Materials selected for the light strip may be set according to requirements in actual operations. The light strips may be set on a surface of the light source. There may be a certain distance between the light strips and the light source, and when the light source illuminates for a long time, heat produced by the light source may be dissipated. The light strips may include a first light strip that produces a first light pattern and a second light strip that produces a second light pattern. The first light pattern may indicate an inhalation state, and the second light pattern may indicate an exhalation state. The illuminating duration of the first light pattern and the second light pattern may be set at a ratio of 1:1.5 to 1:2. For example, the illuminating duration of the first light pattern may last for 0.8 seconds, and the illuminating duration of the second light pattern may last for 1.2 seconds. As another example, the first light pattern may last for 0.8 seconds, and the second light pattern may last for 1.5 seconds. The settings of the first light pattern and the second light pattern may be adjusted according to a status of the subject.

In some embodiments, the breathing guiding apparatus 100 may include the light source. The breathing guiding apparatus 100 may have a simple structure, a mature design, and a convenient installation. The breathing guiding apparatus 100 may be capable of implementing the function that guides the subject to breathe regularly. The breathing guiding apparatus 100 may adjust a variable rate of the breathing in real-time, according to a specific status of the subject so as to achieve an optimality state. In some embodiments, breathing patterns corresponding to various types of subjects may be pre-stored. For example, the various types herein may be defined according to the gender and/or the age of the subject. In a scanning process, the rate at which the breathing guiding apparatus 100 directs the subject to breathe may be consistent with the pre-stored breathing pattern corresponding to the subject. In some embodiments, a breathing examination device, such as a pressure sensor, may be used to detect the breathing pattern of the subject in first several breathing cycles in real time. The breathing pattern of the subject may be determined according to the breathing pattern detected in the first several breathing cycles, and the rate at which the breathing guiding apparatus 100 directs the subject to breathe may be set to be consistent with the determined breathing pattern. In other embodiments, the breathing guiding apparatus 100 may also have other configurations. For example, the breathing guiding apparatus 100 may be a signal generating device that taps at a certain frequency. The breathing guiding apparatus 100 may guide the subject to breathe regularly so as to reduce motion artifacts of X-ray imaging.

In some embodiments, the first light pattern and the second light pattern may characterize two displaying states of the light source. For example, the inhalation state may correspond to the first light pattern, and the light source may illuminate gradient yellow lights. The gradient yellow lights change from a light color to a dark color gradually. When the yellow lights change to a darkest color, the inhalation of the subject may end. The exhalation state may correspond to the second light pattern, and the light source also may illuminate gradient yellow light. The gradient yellow lights change from a dark color to a light color gradually. When the yellow lights change to a lightest color, the exhalation of the subject may end. The first light pattern and the second light pattern may also be set to different gradient colors so as to differentiate the inhalation state and the exhalation state of the subject.

In some embodiments, the duration of the first light pattern and the second light pattern may have a ratio of 1:1.75. The light pattern may be realized by a light strip. The light strips may include a first light strip that produces the first light pattern and a second light strip that produces the second light pattern. For example, the light strips are transparent. The first light strip may be transparent for light yellow lights. The second light strip may be transparent for a soft blue light. The controller 300 may control the time period during which the light source emits lights of different colors to realize the illumination of the first light pattern and the second light pattern in different time periods. For example, the controller 300 may control the light source to emit light yellow lights during the time period T1, and the breathing guiding apparatus 100 may guide the subject to inhale during the time period T1. Similarly, the controller 300 may control the light source to emit soft blue light during the time period T2, and the breathing guiding apparatus 100 may guide the subject to exhale during the time period of T2. The controller 300 may control the X-ray generator 200 to generate X-rays after the breathing state of the subject becomes regular, and a scanning image may be generated.

In the above embodiments, a specific technical solution is described to enable the breathing guiding apparatus 100 to provide different states for guiding the breathing of the subject more easily. The breathing guiding apparatus 100 may guide the subject to breathe in a regular state. The breathing guiding apparatus 100 may enable the guidance of the breathing state based on the light source and the light pattern. During a breathing guiding process, the ratio of the inhalation state to the exhalation state may be set according to different types of subjects. Light-out signals of the first light pattern and the second light pattern on a time axis may be recorded, and scanning data of the subject may also be recorded in real-time. In an ideal case, if information of the first light pattern and the second light pattern is consistent with the breathing state of the subject, image reconstruction may be performed.

In some embodiments, the light patterns may be set to be activated alternatively, in forms of repetitions. For example, the first light pattern may be activated first, and the subject be guided to inhale. The second light pattern may be activated after the first light pattern is turned off, and the subject may be guided to exhale. The first light pattern and the second light pattern may be activated by turns. In some embodiments, the lights of the first light pattern change from weak to strong, and the lights of the second light pattern change from strong to weak. The first light pattern directs the subject to inhale, and the second light pattern directs the subject to exhale. The light intensity of the light source may vary due to a voltage change of the light source or other means to achieve the purpose of guiding the subject to breathe regularly. Specifically, the first light pattern may be set to vary from weak to strong, and when the lights of the first light pattern become strongest, the inhalation ends. The second light pattern may be set to vary from strong to weak, and when the lights of the second light pattern become weakest, the exhalation ends. The subject may be guided to breathe regularly by the breathing guiding apparatus 100. At an end of each inhalation and exhalation, the X-ray generator 200 may be controlled by the controller 300 to generate X-rays to scan the subject.

In some embodiments, in consideration of the sensual experience of the subject, a visual impact on the subject may be reduced, and the light pattern may be set to a gradient form. The gradient light pattern may capture intervals between inhalations and exhalations of the subject more accurately. In some embodiments, a processor may determine a breathing cycle of the subject according to the first light pattern and the second light pattern, thereby determining an X-ray scanning window, for example, irradiating X-rays at an end of an exhalation or inhalation, and a scanning image of the subject may be generated. The motion artifacts caused by breathing may be reduced, thus generating a more clear scanning image.

In some embodiments, the medical examination system 10 may further include a breathing synchronization detection apparatus 400. The breathing synchronization detection apparatus 400 is coupled to the controller 300, for example, through an electrical connection. The breathing synchronization detection apparatus 400 may be configured to detect whether the breathing state of the subject is consistent with a breath guiding state generated by the breathing guiding apparatus 100. The controller 300 may control the X-ray generator 200 to scan the subject if the breathing synchronization detection apparatus 400 detects that the frequency of the breathing of the subject is consistent with or within a certain threshold range of the breathing guiding state generated by the breathing guiding apparatus 100.

In the above embodiments, if the breathing synchronization detection apparatus 400 detects that the frequency of the breathing is consistent with or within a certain threshold range of the breath guiding state generated by the breathing guiding apparatus 100, it may indicate that the breathing of the subject is uniform and regular. The X-ray generator 200 may be configured to be under a radiation mode with an uniform radiation window, to have X-ray images. The breathing synchronization detection apparatus 400 may include a breath examination unit and a judgment unit. In some embodiments, the breath examination unit may be used to detect a real-time breathing state of the subject. For example, the breath examination unit may include a sensitive breath sensor. The judgment unit may be configured to determine whether a detected breathing signal of the subject is consistent with or within a preset threshold range of a breath guiding state. For example, the breath examination unit of the breathing synchronization detection apparatus 400 may include a patch sensor. The patch sensor may be set on a surface of the patient support 102 of the medical examination system 10. In some embodiments, the breath examination unit of the breathing synchronization detection apparatus 400 may include an image acquiring device. Merely by ways of example, the image acquiring device may be set on an inner side wall of the slip ring 101 of the medical examination system 10. The image acquiring device may include a plurality of cameras. The plurality of cameras may generate real-time breathing signal through a multi-angle human body inspection. The judgment unit of the breathing synchronization detection apparatus 400 may determine whether the real-time breathing signal is consistent with or within a preset threshold range of the breath guiding state of the breathing guiding apparatus 100. The breath detecting unit of the breathing synchronization detection apparatus 400 may be capable of detecting data of vital signs such as the breathing of a patient. The detected data of vital signs may be compared with data of the breathing guiding apparatus 100. If the two types of data are matched, the breathing synchronization detection apparatus 400 may send a command to the controller 300. After the controller 300 receives the command, the controller 300 may send a control signal to the X-ray generator 200 to generate X-rays.

In some embodiments, the settings of the breathing synchronization detection apparatus 400 may facilitate the achievement of a sufficient examination effect of the breathing guiding apparatus 100. The breathing synchronization detection apparatus 400 may send a command to the controller 300 when the breathing state of the subject is consistent with the breath guiding state of the breathing guiding apparatus 100. Further, the controller 300 may send a control signal to the X-ray generator 200 to control the X-ray generator 200 to emit X-rays, such that the medical examination system 10 may generate an image. When the controller 300 receives the command sent by the breathing synchronization detection apparatus 400, the X-ray generator 200 may keep emitting X-rays throughout the image acquisition process. In some embodiments, when the controller 300 receives the command sent by the breathing synchronization detection apparatus 400, the X-ray generator 200 may emit X-rays in specific phases according to signals detected by the breath detecting unit or signals of the breathing guiding apparatus 100.

Referring to FIG. 2, a medical examination method is provided according to some embodiments of the present disclosure. The medical examination method may include a plurality of operations in S10 through S30.

In S10, a first light pattern guiding a subject to inhale and a second light pattern guiding the subject to exhale may be generated by the breathing guiding apparatus 100. The breathing guiding apparatus 100 may be configured to guide the subject to breathe regularly, with a fixed frequency. The specific structure of the breathing guiding apparatus 100 may be set as needed. And durations of the first light pattern and the second light pattern may be set according to actual application requirements.

In S20, the X-ray generator 200 may be controlled to generate X-rays during the subject breath regularly. The X-ray generator 200 may be configured to generate X-rays to complete the scanning of the subject. In some embodiments, the emission of the X-rays from the X-ray generator 200 may be controlled in accordance with operations of the medical examination system 10.

In S30, an image of the subject scanned by the X-ray generator 200 may be generated and then processed by an image reconstruction method. Motion artifacts in the image may be reduced by performing an imaging scan in accordance with a periodical breathing cycle of the subject. When the subject is in a periodically breathing state, the X-ray generator 200 may acquire a plurality of images. After images with apparent motion artifacts are removed, other images may be recombined so as to obtain a static medical examination image of the subject. In some embodiments, the medical examination method includes: generating a first light pattern guiding a subject to inhale and a second light pattern guiding the subject to exhale; controlling an X-ray generator to generate X-rays during the subject breathe regularly; generating an image of the subject, and reconstructing and processing images.

In some embodiments, the subject may be guided to breathe at a fixed rhythm by setting the breathing guiding apparatus 100. In some embodiments, the X-ray generator 200 may be controlled to perform X-ray scanning on the subject after the subject enters a regular breathing state. The generated images may need to be classified and filtered so as to remove images with motion artifacts, making the examination results more stable and reliable.

In some embodiments, after the subject adjusts the frequency of breathing, and the medical examination system 10 detects that the breathing of the subject enters a steady state, the X-ray generator 200 may be controlled to perform an X-ray scanning. The steady state of the breathing of the subject may be captured. The steady state used herein may refer to a state at an end of an exhalation of the subject. In addition, the steady state may also refer to a steady state of the inhalation end time of the subject. The X-ray scanning may be performed under the steady state so as to reduce motion artifacts caused by the breathing of the subject, which makes the examination result more stable and reliable.

In some embodiment, operations in S10 further includes detecting whether the breathing state of the subject is consistent with the breath guiding state generated by the breathing guiding apparatus 100 in S110.

If the breathing state of the subject is consistent with the breath guiding state generated by the breathing guiding apparatus 100, the process may proceed to S20. If the breathing state of the subject is inconsistent with the breath guiding state generated by the breathing guiding apparatus 100, the subject may be guided to adjust breathe according to the breath guiding state of the breathing guiding apparatus 100 until the breathing state of the subject is consistent with the breath guiding state generated by the breathing guiding apparatus 100, then the process may proceed to S20.

In the above embodiment, a breathing synchronization detection apparatus 400 may be provided. The breathing synchronization detection apparatus 400 may include a breath examination unit and a judgment unit, the breath examination unit may be used to detect a real-time breathing state of the subject. For example, the breath examination unit may include a sensitive breath sensor.

The judgment unit may be configured to determine whether a detected breathing signal of the subject is consistent with or within a preset threshold range of a breath guiding state. If the breathing state of the subject is consistent with the breath guiding state generated by the breathing guiding apparatus 100, the process may proceed to S20.

For example, the breath examination unit of the breathing synchronization detection apparatus 400 may include a patch sensor. The patch sensor may be set on a surface of the patient support 102 of the medical examination system 10. In some embodiments, the breath examination unit of the breathing synchronization detection apparatus 400 may include an image acquisition device. Merely by ways of example, the image acquiring device may be set on an inner side wall of the slip ring 101 of the medical examination system 10. The image acquiring device may include a plurality of cameras. The plurality of cameras may recognize real-time breathing signal through a multi-angle human body inspection. The judgment unit of the breathing synchronization detection apparatus 400 may determine whether the real-time breathing signal is consistent with or within a preset threshold range of the breath guiding state of the breathing guiding apparatus 100. The breath detecting unit of the breathing synchronization detection apparatus 400 may be capable of detecting data of vital signs such as the breathing of a patient. The detected data of vital signs may be compared with data of the breathing guiding apparatus 100, and if the two types of data are matched, the breathing synchronization detection apparatus may send a command to the controller 300. After receiving the control signal, the controller 300 further sends a control signal for the X-ray generator 200.

In some embodiments, in S110, when the breathing state of the subject is consistent with the breath guiding state generated by the breathing guiding apparatus 100, the medical examination method may further include operations in S120. In S120, the controller 300 may control the X-ray generator 200 to generate X-rays at a time point when a first light pattern and/or a second light pattern end.

The controller 300 may control the X-ray generator 200 to scan the subject at the end of the first light pattern and the second light pattern. The time points when the first light pattern and the second light pattern end may be time points when an exhalation and an inhalation end. At the time points when an exhalation and an inhalation end, the subject may be in a relatively stationary state, and motion artifacts may be reduced if the subject is imaged at these time points.

In some embodiments, the breathing frequency of the subject may be detected by the breathing synchronization detection apparatus 400. The controller 300 may control the X-ray generator 200 to scan the subject if the breathing synchronization detection apparatus 400 detects that the frequency of the breathing of the subject is consistent with or within a certain threshold range of the breathing guiding state generated by the breathing guiding apparatus 100. The X-ray generator 200 may emit X-rays at time points when an exhalation and/or an inhalation ends. That is, the X-ray generator 200 may be controlled to generate X-rays at the time when the first light pattern and/or the second light pattern end, which makes images acquired by the medical examination method more uniform and reliable. In some embodiments, in S10, the durations of the first light pattern and the second light pattern may be set according to a ratio ranging from 1:1.5 to 1:2. For example, the durations of the first light pattern and the second light pattern may be set according to a ratio ranging from 1:1.5 to 1:2. Those skilled in the art may understand that if the breathing synchronization detection apparatus 400 detects that the frequency of breathing is consistent with or within a certain threshold range of the breath guiding state generated by the breathing guiding apparatus 100, the X-ray generator 200 may also keep irradiating X-rays during a plurality of cycles of exhalation and inhalation.

In some embodiments, in S10, the first light pattern and the second light pattern be activated alternatively. If the breathing guiding apparatus 100 guides the subject to breathe regularly, X-ray scanning at a time point when the first light pattern ends may reduce motion artifacts in the examination result.

In some embodiment, in S10, the lights of the first light pattern change from weak to strong, and the lights of the second light pattern change from strong to weak. Specifically, the first light pattern may be set to vary from weak to strong, and when the lights of the first light pattern become strongest, the inhalation ends. And the second light pattern is set to be strong to weak, and when the light is weakest, the exhalation ends. The subject may be guided to breathe regularly by the breathing guiding apparatus 100. In consideration of the sensual experience of the subject, a visual impact on the subject may be reduced, and the light pattern may be set to a gradient form. The gradient light pattern may capture intervals between inhalations and exhalations of the subject more accurately. At the time interval in which the exhalation or inhalation ends, X-ray irradiation is performed to acquire the medical examination image of the subject by the X-ray irradiation. In this embodiment, motion artifacts caused by breathing is reduced, making the medical examination image clearer.

Figure 3:
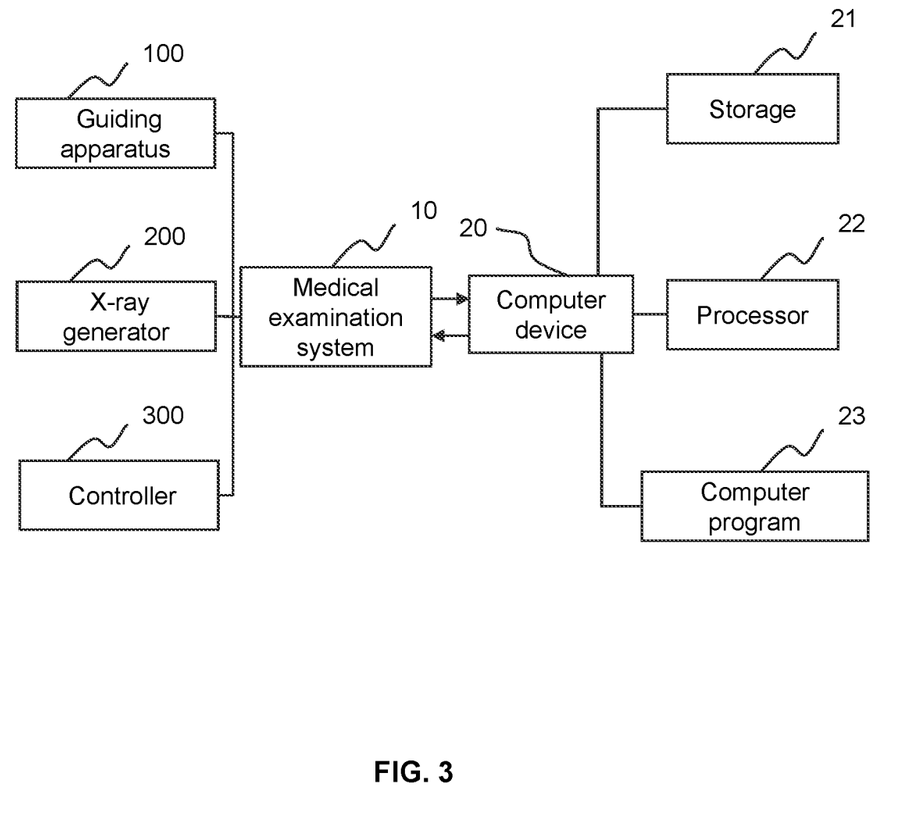
FIG. 3 is a schematic diagram of a computing device according to some embodiments of the present disclosure.

Referring to FIG. 3, a computing device 20 is provided according to some embodiments of the present disclosure. The computing device may include a storage 21, a processor 22, and computer programs 23 stored on the storage 21 and executable by the processor 22. The processor 22 may execute the computer programs 23 to implement the operations of the medical examination method mentioned above.

The medical examination method performed by the processor 22 may include the following operations.

In S10, a first light pattern guiding a subject to inhale and a second light pattern guiding the subject to exhale may be generated by the breathing guiding apparatus 100.

In S20, the X-ray generator 200 may be controlled to generate X-rays during the subject breath regularly.

In S30, an image of the subject scanned by the X-ray generator 200 may be obtained, and then reconstructed.

In some embodiments, after S10, the method may further include:

S110, a determination may be made as to whether the breathing state of the subject is consistent with the breath guiding state generated by the breathing guiding apparatus. If the determination result being that the breathing state of the subject is consistent with the breath guiding state generated by the breathing guiding apparatus, the X-ray generator may be controlled to generate X-rays.

If the breathing state of the subject is consistent with the breath guiding state generated by the breathing guiding apparatus 100, the process may proceed to S20. If the breathing state of the subject is inconsistent with the breath guiding state generated by the breathing guiding apparatus 100, the subject may be guided to adjust breathe according to the breath guiding state of the breathing guiding apparatus 100 until the breathing state of the subject is consistent with the breath guiding state generated by the breathing guiding apparatus 100, then the process may proceed to S20.

In some embodiments, in the step S110, when the breathing state of the subject is consistent with the breathing state generated by the breathing guiding apparatus 100, the medical examination method may further include:

S120, the determination result being that the breathing state of the subject is consistent with the breath guiding state generated by the breathing guiding apparatus, controlling the X-ray generator to generate X-rays at time points when at least one of the first light pattern or the second light pattern ends. Alternatively, during a plurality of exhalation cycles and inhalation cycles, irradiation of the X-ray generator 200 may be uninterrupted.

To address the problem listed above, in some embodiments, a computer readable storage medium may be provided for storing computer programs that, when executed by a processor, implements the operations of the medical examination method.

Those skilled in the art may understand that all or part of the process in implementing the method of the embodiment may be accomplished by a computer program instructing the associated hardware. The computer program can be stored in a non-volatile computer-readable storage medium, which, when executed, can include the flow of an embodiment of the methods. Wherein, any references to a storage device, storage, databases, or other media used in the various embodiments provided by the present disclosure may include a non-volatile and/or volatile storage device. Non-volatile storage may include read-only storage (ROM), programmable ROM (PROM), electrically programmable ROM (EPROM), electrically erasable programmable ROM (EEPROM), or flash memory. Volatile storage can include random access storage (RAM) or external cache storage. By way of illustration and not limitation, RAM is available in a variety of forms, such as static RAM (SRAM), dynamic RAM (DRAM), synchronous DRAM (SDRAM), double data rate SDRAM (DDRSDRAM), enhanced SDRAM (ESDRAM), synchronous link (Synchlink) DRAM (SLDRAM), storage bus (Rambus) direct RAM (RDRAM), direct storage bus dynamic RAM (DRDRAM), and storage bus dynamic RAM (RDRAM).

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A medical examination system, comprising:
    a breathing guiding apparatus configured to guide a breathing of a subject;
    an imaging device configured to scan the subject; and
    a controller coupled to the breathing guiding apparatus and configured to cause the breathing guiding apparatus to generate a breath guiding state for guiding the breathing of the subject based on a breathing pattern defined according to gender or age of the subject.

2. The medical examination system of claim 1, wherein the breathing guiding apparatus includes a light source electrically connected to the controller, the light source being configured to generate, under the control of the controller, lights that guide the breathing of the subject.

3. The medical examination system of claim 1, wherein the controller is configured to activate the imaging device based on time determined by the breathing guiding apparatus.

4. The medical examination system of claim 1, further including a breathing synchronization detection apparatus coupled to the controller, the breathing synchronization detection apparatus being configured to detect whether the breathing of the subject is consistent with the breath guiding state generated by the breathing guiding apparatus.

5. The medical examination system of claim 4, wherein the breathing synchronization detection apparatus includes a sensor configured to sense the breathing of the subject when the subject is at a scanning position.

6. The medical examination system of claim 4, wherein the breathing synchronization detection apparatus further includes an image acquisition device.

7. The medical examination system of claim 6, further comprising a slip ring, wherein the image acquisition device is set on an inner side wall of the slip ring.

8. The medical examination system of claim 4, wherein the imaging device includes an X-ray generator, the controller is coupled to the X-ray generator, and the X-ray generator is configured to emit X-rays at a time point when an inhalation or an exhalation of the subject ends.

9. The medical examination system of claim 8, further comprising a slip ring, wherein the X-ray generator is amounted on the slip ring.

10. A method implemented on a computing device having at least one processor and at least one computer-readable storage device, wherein the method comprising:
- generating a first light pattern guiding a subject to inhale and a second light pattern guiding the subject to exhale based on a breathing pattern defined according to gender or age of the subject;
- causing an imaging device to image the subject when the subject breathes under a guidance of the first light pattern and the second light pattern; and
- generating an image of the subject based on data of the subject generated by the imaging device.

11. The method of claim 10, wherein the imaging device includes an X-ray detector, the method further comprising:
- obtaining a determination result by detecting whether breathing of the subject is consistent with a breath guiding state generated by a breathing guiding apparatus; and
- in response to a determination result that the breathing of the subject is consistent with the breath guiding state generated by the breathing guiding apparatus, controlling the X-ray generator to generate X-rays.

12. The method of claim 11, further comprising:
- in response to a determination result that the breathing of the subject is inconsistent with the breath guiding state generated by the breathing guiding apparatus, instructing the subject to adjust the breathing according to the breathing guiding state until the breathing of the subject becomes consistent with the breath guiding state generated by the breathing guiding apparatus; and
- controlling the X-ray generator to generate X-ray.

13. The method of claim 12, further comprising:
- in response to a determination result that the breathing of the subject is consistent with the breath guiding state generated by the breathing guiding apparatus, causing the X-ray generator to generate X-rays at time points when at least one of the first light pattern or the second light pattern ends.

14. The method of claim 10, wherein a ratio of a duration of the first light pattern to a duration of the second light pattern ranges from 1:1.5 to 1:2.

15. The method of claim 10, wherein the first light pattern and the second light pattern are activated alternately.

16. The method of claim 10, wherein a strength of the first light pattern changes from weak to strong, and a strength of the second light pattern changes from strong to weak.

17. A computing device, comprising:
storage,
- a processor, and
- computer programs stored in the storage and executable by the processor, wherein the processor executes the computer programs to implement operations including:
  - generating a first light pattern guiding a subject to inhale and a second light pattern guiding the subject to exhale based on a breathing pattern defined according to gender or age of the subject;
  - causing an imaging device to image the subject when the subject breathes under a guidance of the first light pattern and the second light pattern; and
  - generating an image of the subject based on data of the subject generated by the imaging device.

18. The computing device of claim 17, wherein the imaging device includes an X-ray detector, the operations further comprising:
- obtaining a determination result by detecting whether breathing of the subject is consistent with a breath guiding state generated by a breathing guiding apparatus; and
- in response to a determination result that the breathing of the subject is consistent with the breath guiding state generated by the breathing guiding apparatus, controlling the X-ray generator to generate X-rays.

19. The computing device of claim 18, the operations further comprising:
- in response to a determination result that the breathing of the subject is inconsistent with the breath guiding state generated by the breathing guiding apparatus, instructing the subject to adjust the breathing according to the breathing guiding state until the breathing of the subject becomes consistent with the breath guiding state generated by the breathing guiding apparatus; and
- controlling the X-ray generator to generate X-ray.

20. The computing device of claim 19, the operations further comprising:
- in response to a determination result that the breathing of the subject is consistent with the breath guiding state generated by the breathing guiding apparatus, causing the X-ray generator to generate X-rays at time points when at least one of the first light pattern or the second light pattern ends.

* * * * *